(12) United States Patent  (10) Patent No.: US 8,604,783 B2
Kruspe et al.  (45) Date of Patent: *Dec. 10, 2013

(54) METHOD AND APPARATUS FOR NMR MEASUREMENTS WHILE DRILLING WITH MULTIPLE DEPTHS OF INVESTIGATION

(75) Inventors: Thomas Kruspe, Wietzendorf (DE); Martin Blanz, Celle (DE)

(73) Assignee: Baker Hughes Incorporated, Houston, TX (US)

( * ) Notice: Subject to any disclaimer, the term of this patent is extended or adjusted under 35 U.S.C. 154(b) by 742 days.

This patent is subject to a terminal disclaimer.

(21) Appl. No.: 12/763,711

(22) Filed: Apr. 20, 2010

(65) Prior Publication Data
US 2010/0283461 A1    Nov. 11, 2010

Related U.S. Application Data

(60) Provisional application No. 61/176,791, filed on May 8, 2009.

(51) Int. Cl.
*G01V 3/00* (2006.01)
*G01V 3/32* (2006.01)

(52) U.S. Cl.
USPC .......................................... 324/303; 324/300

(58) Field of Classification Search
USPC .............................................. 324/303; 702/8
See application file for complete search history.

(56) References Cited

U.S. PATENT DOCUMENTS

| 4,717,877 | A | * | 1/1988 | Taicher et al. | 324/303 |
|---|---|---|---|---|---|
| 6,215,304 | B1 | | 4/2001 | Slade | |
| 6,246,236 | B1 | * | 6/2001 | Poitzsch et al. | 324/303 |
| 6,518,758 | B1 | | 2/2003 | Speier et al. | |
| 6,528,995 | B1 | | 3/2003 | Speier et al. | |
| 6,769,497 | B2 | | 8/2004 | Dubinsky et al. | |
| 6,933,719 | B2 | | 8/2005 | Thomann et al. | |
| 7,372,263 | B2 | | 5/2008 | Edwards | |
| 8,330,459 | B2 | * | 12/2012 | Kruspe et al. | 324/303 |
| 2002/0175681 | A1 | * | 11/2002 | Taicher | 324/303 |
| 2009/0091320 | A1 | * | 4/2009 | Flaum et al. | 324/303 |

* cited by examiner

*Primary Examiner* — Jermele M Hollington
*Assistant Examiner* — Emily Chan
(74) *Attorney, Agent, or Firm* — Cantor Colburn LLP

(57) ABSTRACT

NMR spin echo signals are measured in a borehole during drilling. Signals measured in a plurality of regions of investigation with different depths of investigation in the borehole are processed to give a radial profile of formation properties, including a potential gas kick.

18 Claims, 6 Drawing Sheets

METHOD AND APPARATUS FOR NMR MEASUREMENTS WHILE DRILLING WITH MULTIPLE DEPTHS OF INVESTIGATION

CROSS-REFERENCE TO RELATED APPLICATIONS

This applications claims priority from U.S. Provisional Patent Application Ser. No. 61/176,791 filed on May 8, 2009. The application is also related to U.S. patent applications being filed concurrently with the present application titled "A method and apparatus for NMR measurements in underbalanced drilling" under Attorney Docket No. NMR4-49302-US, and titled "A method and apparatus for NMR measurements while drilling in small boreholes" under Attorney Docket No. NMR4-50756-US.

BACKGROUND OF THE DISCLOSURE

1. Field of the Disclosure

The present disclosure relates generally to determining geological properties of subsurface formations using Nuclear Magnetic Resonance ("NMR") methods for logging wellbores, particularly for correcting for the effects of fluid flow during underbalanced drilling on NMR signals.

2. Description of the Related Art

A variety of techniques are currently utilized in determining the presence and estimation of quantities of hydrocarbons (oil and gas) in earth formations. These methods are designed to determine formation parameters, including among other things, the resistivity, porosity and permeability of the rock formation surrounding the wellbore drilled for recovering the hydrocarbons. Typically, the tools designed to provide the desired information are used to log the wellbore. Much of the logging is done after the well bores have been drilled. More recently, wellbores have been logged while drilling, which is referred to as measurement-while-drilling (MWD) or logging-while-drilling (LWD).

One commonly used technique involves utilizing Nuclear Magnetic Resonance (NMR) logging tools and methods for determining, among other things, porosity, hydrocarbon saturation and permeability of the rock formations. The NMR logging tools are utilized to excite the nuclei of the fluids in the geological formations surrounding the wellbore so that certain parameters such as nuclear spin density, longitudinal relaxation time (generally referred to in the art as $T_1$) and transverse relaxation time (generally referred to as $T_2$) of the geological formations can be measured. From such measurements, porosity, permeability and hydrocarbon saturation are determined, which provides valuable information about the make-up of the geological formations and the amount of extractable hydrocarbons.

The NMR tools generate a static magnetic field in a region of interest surrounding the wellbore. NMR is based on the fact that the nuclei of many elements have angular momentum (spin) and a magnetic moment. The nuclei have a characteristic Larmor resonant frequency related to the magnitude of the magnetic field in their locality. Over time the nuclear spins align themselves along an externally applied static magnetic field creating a macroscopic magnetization, in short: magnetization. This equilibrium situation can be disturbed by a pulse of an oscillating magnetic field, which tips the spins with resonant frequency within the bandwidth of the oscillating magnetic field away from the static field direction. The angle θ through which the spins exactly on resonance are tipped is given by the equation:

$$\theta = \gamma B_1 t_p / 2 \quad (1)$$

where γ is the gyromagnetic ratio, $B_1$ is the magnetic flux density amplitude of the sinusoidally oscillating field and $t_p$ is the duration of the RF pulse.

After tipping, the magnetization precesses around the static field at a particular frequency known as the Larmor frequency $\omega_0$ given by $$\omega_0 = \gamma B_0 \quad (2)$$

where $B_0$ is the static magnetic flux density. For hydrogen nuclei γ/2π=4258 Hz/Gauss, so that a static field of 235 Gauss would produce a precession frequency of 1 MHz. At the same time, the magnetization returns to the equilibrium direction (i.e., aligned with the static field) according to a characteristic recovery time known as the "spin-lattice relaxation time" or $T_1$. $T_1$ is controlled by the molecular environment and is typically one millisecond to several seconds in rocks.

At the end of a θ=90° tipping pulse, spins on resonance are pointed in a common direction perpendicular to the static field, and they precess at the Larmor frequency. However, because of inhomogeneity in the static field due to the constraints on tool shape, imperfect instrumentation, or microscopic material heterogeneities, each nuclear spin precesses at a slightly different rate. Hence, after a time long compared to the precession period, but shorter than $T_1$, the spins will no longer be precessing in phase. This de-phasing occurs with a time constant that is commonly referred to as $T_2^*$. Dephasing due to static field inhomogeneity can be recovered by generating spin echoes (see below). The remaining dephasing is characterized by the time constant $T_2$ and is due to properties of the material.

A receiving coil is designed so that a voltage is induced by the precessing spins. Only that component of the nuclear magnetization precesses that is orthogonal to the static magnetic field. The precessing component induces a signal in the receiving coil if its orientation is appropriate. After a 180° tipping pulse (an "inversion pulse"), the spins on resonance are aligned opposite to the static field and the magnetization relaxes along the static field axis to the equilibrium direction. Hence, a signal will be generated after a 90° tipping pulse, but not after a 180° tipping pulse in a generally uniform magnetic field.

While many different methods for measuring $T_1$ have been developed, a single standard known as the CPMG sequence (Carr-Purcell-Meiboom-Gill) for measuring $T_2$ has evolved. In contrast to laboratory NMR magnets, well logging tools have inhomogeneous magnetic fields due to the constraints on placing the magnets within a tubular tool and the inherent "inside-out" geometry. Maxwell's divergence theorem dictates that there cannot be a region of high homogeneity outside the tool. Therefore in typical well bores, $T_2^* \ll T_2$, and the free induction decay becomes a measurement of the apparatus-induced inhomogeneities. To measure the true $T_2$ in such situations, it is necessary to cancel the effect of the apparatus-induced inhomogeneities. To accomplish the same, a series of pulses is applied to repeatedly refocus the spin system, canceling the $T_2^*$ effects and forming a series of spin echoes. The decay of echo amplitude is a true measure of the decay due to material properties. Furthermore it can be shown that the decay is in fact composed of a number of different decay components forming a $T_2$ distribution. The echo decay data can be processed to reveal this distribution which is related to rock pore size distribution and other parameters of interest to the well log analyst.

Normally, drilling operations are carried out with a mud weight selected so that the fluid pressure in the borehole is slightly greater than the formation fluid pressure. Potential risks associated with normal drilling are formation damage (when borehole fluid flows uncontrollably into the formation) and lost circulation. The problem of lost circulation can be particularly acute in highly fractured carbonate reservoirs. In underbalanced drilling, the fluid pressure in the borehole is less than the formation pore pressure. By maintaining the underbalanced state, the risk of formation damage is reduced and lost circulation will not happen. In addition, an increased rate of penetration (ROP) is possible and, in addition, the risk of differential sticking is also reduced.

When underbalanced drilling is done, there will be inflow of formation fluid into the borehole. The amount of fluid inflow depends on fluid viscosity, formation permeability and pressure difference between borehole and formation. In certain cases substantial fluid-velocities can be expected. The flow is in radial direction towards the borehole wall. The NMR measurements of conventional NMR tools with high radial magnetic field gradient will be influenced by the motion of the fluid molecules towards the borehole. The present disclosure addresses this problem of fluid inflow.

SUMMARY OF THE DISCLOSURE

One embodiment of the disclosure is an apparatus configured to evaluate an earth formation. The apparatus includes: a carrier configured to be conveyed in a borehole in the earth formation; a magnet assembly on the carrier configured to produce a static magnetic field in the earth formation and define a plurality of regions at different radial distance from the borehole; at least one antenna on the carrier configured to be activated with at least one pulse sequence, the at least one pulse sequence configured to produce a signal from nuclear spins from an associated one of the plurality of regions of examination; and a processor configured to estimate a value of a property of the earth formation at the different radial distances using the produced signal from each of the plurality of regions of examination.

Another embodiment of the disclosure is a method of evaluating an earth formation. The method includes: conveying a carrier into a borehole in the earth formation; using a magnet assembly on the carrier for producing a static magnetic field in the earth formation and defining a plurality of regions at different radial distance from the borehole; activating at least one antenna on the carrier with at least one pulse sequence, the at least one pulse sequence configured to produce a signal from nuclear spins from an associated one of the plurality of regions of examination; and using a processor for estimating a value of a property of the earth formation at the different radial distances using the produced signal from each of the plurality of regions of examination.

Another embodiment of the disclosure is a computer-readable medium product having stored thereon instructions that when executed by a processor cause the processor to execute a method. The method includes: estimating a value of a property of the earth formation at each of a plurality of regions of examination at different radial distances from a borehole using signals produced signal from each of the plurality of regions of examination responsive to activation of at least one antenna with at least one pulse sequence, the at least one pulse sequence configured to produce a signal from nuclear spins from an associated one of the plurality of regions of examination.

BRIEF DESCRIPTION OF THE DRAWINGS

The present disclosure is best understood with reference to the accompanying figures in which like numerals refer to like elements and in which.

DETAILED DESCRIPTION OF THE DISCLOSURE

Figure 1:
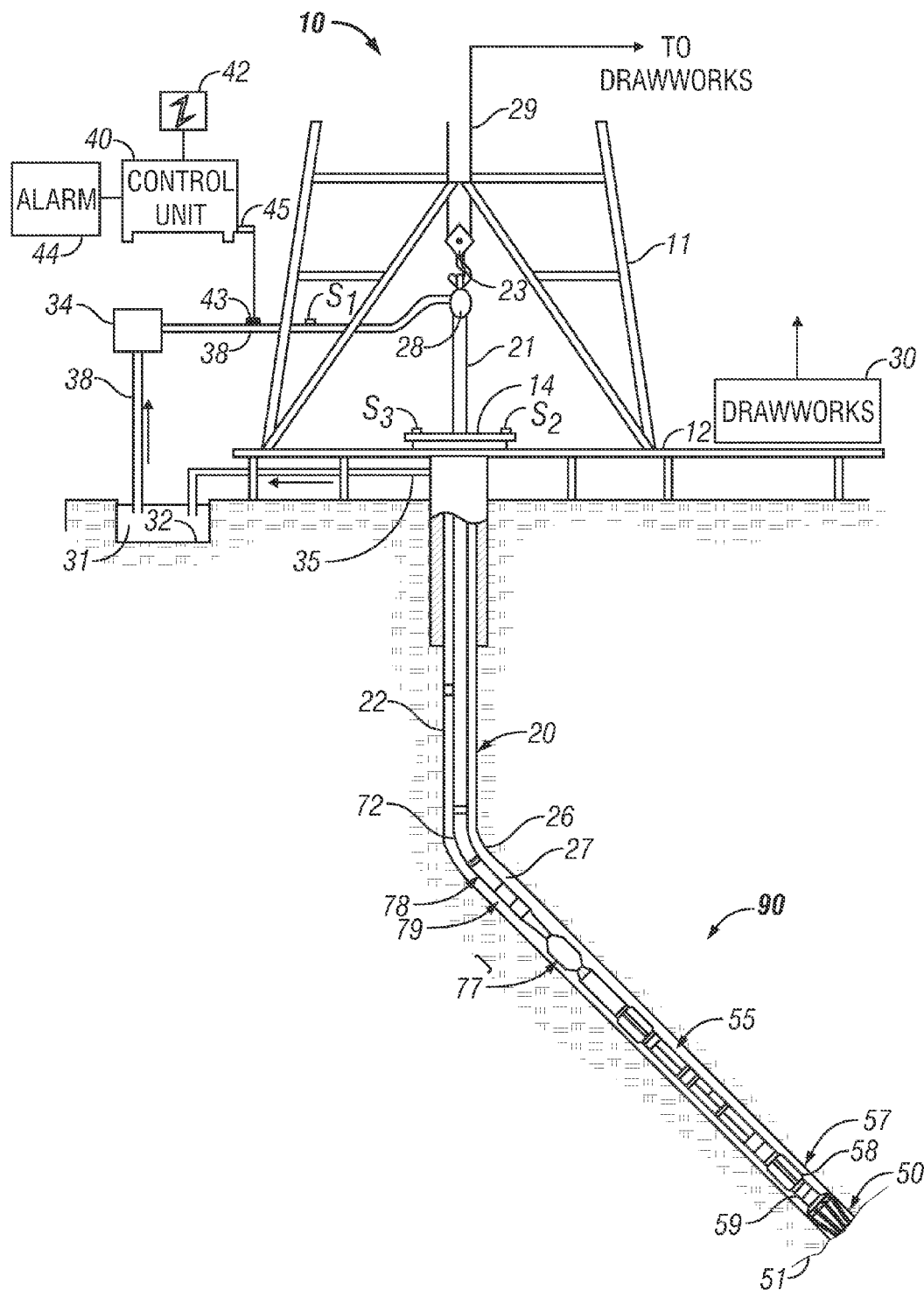
FIG. 1 shows a measurement-while-drilling tool suitable for use with the present disclosure.

FIG. 1 shows a schematic diagram of a drilling system 10 with a drillstring 20 carrying a drilling assembly 90 (also referred to as the bottomhole assembly, or "BHA") conveyed in a "wellbore" or "borehole" 26 for drilling the wellbore. The drilling system 10 includes a conventional derrick 11 erected on a floor 12 which supports a rotary table 14 that is rotated by a prime mover such as an electric motor (not shown) at a desired rotational speed. The drillstring 20 includes a tubing such as a drill pipe 22 or a coiled-tubing extending downward from the surface into the borehole 26. The drillstring 20 is pushed into the wellbore 26 when a drill pipe 22 is used as the tubing. For coiled-tubing applications, a tubing injector, such as an injector (not shown), however, is used to move the tubing from a source thereof, such as a reel (not shown), to the wellbore 26. The drill bit 50 attached to the end of the drillstring breaks up the geological formations when it is rotated to drill the borehole 26. If a drill pipe 22 is used, the drillstring 20 is coupled to a drawworks 30 via a Kelly joint 21, swivel 28, and line 29 through a pulley 23. During drilling operations, the drawworks 30 is operated to control the weight on bit, which is an important parameter that affects the rate of penetration. The operation of the drawworks is well known in the art and is thus not described in detail herein. For the purposes of this disclosure, it is necessary to know the axial velocity (rate of penetration or ROP) of the bottomhole assembly. Depth information and ROP may be communicated downhole from a surface location. Alternatively, the method disclosed in U.S. Pat. No. 6,769,497 to Dubinsky et al. having the same assignee as the present application and the contents of which are incorporated herein by reference may be used. The method of Dubinsky uses axial accelerometers to determine the ROP. During drilling operations, a suitable drilling fluid 31 from a mud pit (source) 32 is circulated under pressure through a channel in the drillstring 20 by a mud pump 34. The drilling fluid passes from the mud pump 34 into the drillstring 20 via a desurger (not shown), fluid line 38 and Kelly joint 21. The drilling fluid 31 is discharged at the borehole bottom 51 through an opening in the drill bit 50. The drilling fluid 31 circulates uphole through the annular space 27 between the drillstring 20 and the borehole 26 and returns to the mud pit 32 via a return line 35. The drilling fluid acts to lubricate the drill bit 50 and to carry borehole cutting or chips away from the drill bit 50. A sensor $S_1$ typically placed in the line 38 provides information about the fluid flow rate. A surface torque sensor $S_2$ and a sensor $S_3$ associated with the drillstring 20 respectively provide information about the torque and rotational speed of the drillstring. Additionally, a sensor (not shown) associated with line 29 is used to provide the hook load of the drillstring 20.

In one embodiment of the disclosure, the drill bit 50 is rotated by only rotating the drill pipe 22. In another embodiment of the disclosure, a downhole motor 55 (mud motor) is disposed in the drilling assembly 90 to rotate the drill bit 50 and the drill pipe 22 is rotated usually to supplement the rotational power, if required, and to effect changes in the drilling direction.

In an exemplary embodiment of FIG. 1, the mud motor 55 is coupled to the drill bit 50 via a drive shaft (not shown) disposed in a bearing assembly 57. The mud motor rotates the drill bit 50 when the drilling fluid 31 passes through the mud motor 55 under pressure. The bearing assembly 57 supports the radial and axial forces of the drill bit. A stabilizer 58 coupled to the bearing assembly 57 acts as a centralizer for the lowermost portion of the mud motor assembly.

In one embodiment of the disclosure, a drilling sensor module 59 is placed near the drill bit 50. The drilling sensor module contains sensors, circuitry and processing software and algorithms relating to the dynamic drilling parameters. Such parameters typically include bit bounce, stick-slip of the drilling assembly, backward rotation, torque, shocks, borehole and annulus pressure, acceleration measurements and other measurements of the drill bit condition. A suitable telemetry or communication sub 72 using, for example, two-way telemetry, is also provided as illustrated in the drilling assembly 90. The drilling sensor module processes the sensor information and transmits it to the surface control unit 40 via the telemetry system 72.

The communication sub 72, a power unit 78 and an MWD tool 79 are all connected in tandem with the drillstring 20. Flex subs, for example, are used in connecting the MWD tool 79 in the drilling assembly 90. Such subs and tools form the bottom hole drilling assembly 90 between the drillstring 20 and the drill bit 50. The drilling assembly 90 makes various measurements including the pulsed nuclear magnetic resonance measurements while the borehole 26 is being drilled. The communication sub 72 obtains the signals and measurements and transfers the signals, using two-way telemetry, for example, to be processed on the surface. Alternatively, the signals can be processed using a downhole processor in the drilling assembly 90.

The surface control unit or processor 40 also receives signals from other downhole sensors and devices and signals from sensors $S_1$-$S_3$ and other sensors used in the system 10 and processes such signals according to programmed instructions provided to the surface control unit 40. The surface control unit 40 displays desired drilling parameters and other information on a display/monitor 42 utilized by an operator to control the drilling operations. The surface control unit 40 typically includes a computer or a microprocessor-based processing system, memory for storing programs or models and data, a recorder for recording data, and other peripherals. The control unit 40 is typically adapted to activate alarms 44 when certain unsafe or undesirable operating conditions occur.

A suitable device for use of the present disclosure is disclosed in U.S. Pat. No. 6,215,304 to Slade, the contents of which are fully incorporated herein by reference. It should be noted that the device taught by Slade is for exemplary purposes only, and the method of the present disclosure may be used with many other NMR logging devices, and may be used for wireline as well as MWD applications.

It should be noted that underbalanced drilling is commonly carried out using a coiled tubing instead of a drillstring. Hence the disclosure of the BHA being conveyed on a drillstring is not to be construed as a limitation. For the purposes of the present disclosure, the term "drilling tubular" is intended to include both a drillstring as well as coiled tubing.

Figure 2:
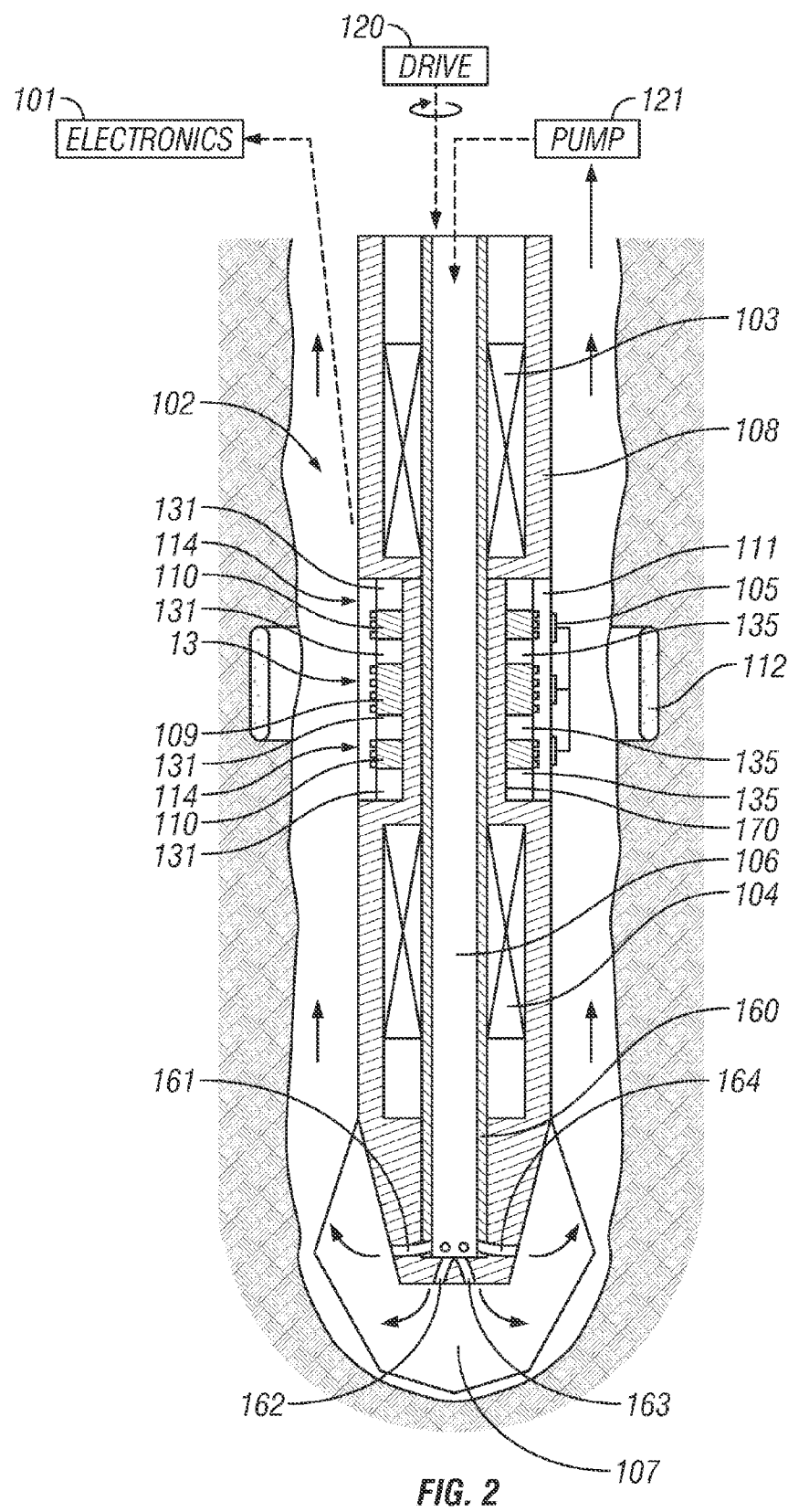
FIG. 2 shows a sensor section of a measurement-while-drilling device suitable for use with the present disclosure.

Referring now to FIG. 2, the tool has a drill bit 107 at one end, a sensor section 102 behind the drill head, and electronics 101. The sensor section 102 comprises a magnetic field generating assembly for generating a $B_0$ magnetic field (which is substantially time invariant over the duration of a measurement), and an RF system for transmitting and receiving RF magnetic pulses and echoes. The magnetic field generating assembly comprises a pair of axially spaced main magnets 103, 104 having opposed pole orientations (i.e. with like magnetic poles facing each other), and three ferrite members 109, 110 axially arranged between the magnets 103, 104. The ferrite members are made of "soft" ferrite which can be distinguished over "hard" ferrite by the shape of the BH curve which affects both intrinsic coercivity ($H_j$, the intersection with the H axis) and initial permeability ($\mu_i$, the gradient of the BH curve in the unmagnetized case). Soft ferrite $\mu_i$ values typically range from 10 to 10000 whereas hard ferrite has $\mu_1$, of about 1. Therefore the soft ferrite has large initial permeability (typically greater than 10, preferably greater than 1000). The RF system comprises a set of RF transmit antenna and RF receive antenna coil windings 105 arranged as a central "field forming" solenoid group 113 and a pair of outer "coupling control" solenoid groups 114.

The tool has a mud pipe 160 with a clear central bore 106 and a number of exit apertures 161-164 to carry drilling mud to the bit 107, and the main body of the tool is provided by a drill collar 108. Drilling mud is pumped down the mud pipe 160 by a pump 121 returning around the tool and the entire tool is rotated by a drive 120. Coiled tubing or a drillstring may be used for coupling the drive to the downhole assembly.

The drill collar 108 provides a recess 170 for RF transmit antenna and RF receive antenna coil windings 105. Gaps in the pockets between the soft ferrite members are filled with non-conducting material 131, 135 (e.g: ceramic or high temperature plastic) and the RF coils 113, 114 are then wound over the soft ferrite members 109, 110. The soft ferrites 109, 110 and RF coil assembly 113, 114 are pressure impregnated with suitable high temperature, low viscosity epoxy resin (not shown) to harden the system against the effects of vibration, seal against drilling fluid at well pressure, and reduce the possibility of magnetoacoustic oscillations. The RF coils 113, 114 are then covered with wear plates 111 typically ceramic or other durable non-conducting material to protect them from the rock chippings flowing upwards past the tool in the borehole mud.

Because of the opposed magnet configuration, the device of Slade has an axisymmetric magnetic field and region of investigation 112 that is unaffected by tool rotation. Use of the ferrite results in a region of investigation that is close to the borehole. This is not a major problem on a MWD tool (except for special situations discussed below that are the focus of this disclosure) because there is little invasion of the formation by borehole drilling fluids prior to the logging. The region of investigation is within a shell with a radial thickness of about 20 mm and an axial length of about 50 mm. The gradient within the region of investigation is less than 2.7 G/cm. It is to be noted that these values are for the Slade device and, as noted above, the method of the present disclosure may also be used with other suitable NMR devices. This field gradient of less than 2.7 G/cm may be considered to be a "near zero" field gradient for the purposes of the present disclosure as discussed below.

Two magnetic fields are used to conduct a typical NMR measurement: a static magnetic field $B_0$ and an alternating magnetic field $B_1$ having a component orthogonal to $B_0$. Pulsed NMR is used in which the alternating field $B_1$ is applied into the sample as a sequence of bursts (usually called pulses):

$$TW-TP-\tau_1-(RP-\tau_2-echo-\tau_2)_n$$

wherein TW is a (long) wait time of usually several times the spin lattice relaxation time, TP is a tipping pulse for tipping the nuclear spins at an angle substantially equal to ninety degrees to cause precession thereof, $\tau_1, \tau_2$ are waiting times, RP is a refocusing pulse for tipping the nuclear spins greater than 90° and n is the number of echoes to be acquired in one sequence. The duration of the events between the echos is called the interecho time TE. The echoes manifest themselves as rotating macroscopic magnetizations and can be detected with a receiver coil. The induced voltages/currents in this coil are the desired NMR signals. In order to obtain NMR signals and refocus them correctly, it is important to adhere to NMR resonance conditions, i.e. $B_0$ and $B_1$ amplitudes as well as pulse phases and shapes need to be chosen correctly as known to people familiar with the art of NMR. An exemplary optimized echo sequence called ORPS is discussed, for example, in Hawkes '013. In the ORPS sequence, the tipping pulse is typically 90°, but the refocusing pulses are less than 180°. This is in contrast to the CPMG sequence in which the refocusing pulses are 180° pulses.

Generally, the geometry of the NMR measurement device gives rise to a volume in the earth formation where the $B_0$ field has the correct strength to fulfill a resonance condition and in which an RF field can be presented with a substantial strength and orientation to reorient nuclear spins within the volume. This volume is often referred to as the sensitive volume. For a tool in motion, as the tool moves axially, the volume containing those protons excited by the excitation pulse (first pulse of the echo sequence) moves away from the sensitive volume. Hence, the number of spins available to contribute to the subsequent NMR signal is reduced with each subsequent echo. As a consequence, those echoes obtained later in an echo sequence with axial tool motion appear small compared to those echoes obtained later in an echo sequence acquired with no tool motion. "Later echoes" does not mean that only the last echoes of a sequence are affected. In fact, the loss of signal starts right at the beginning of a sequence and develops over time in a unique pattern. This phenomenon is called outflow.

In general, NMR echo sequences are repeated several times for the purpose of increasing the final signal-to-noise ratio. Even without concern over signal-to-noise ratio, an echo sequence is usually repeated at least once in order to form a phase-alternated pair (PAP) for the purpose of removing offset and ringing effects.

At the end of a sequence obtained with axial tool motion, the magnetization of the sensitive volume is substantially zero. A wait time TW during which re-magnetization of the formation occurs is used as part of the sequence of pulses. Choosing a wait time of at least 5 times the longest $T_1$ of the formation ensures that the formation is fully magnetized (>99% magnetization) immediately prior to the excitation pulse of the ensuing sequence. However, shorter wait times are often chosen in order to achieve a higher NMR data rate, leading to an improved axial resolution or signal-to-noise ratio. The drawback of shortening TW is that the formation may not be fully magnetized immediately prior to the ensuing sequence. As a consequence, the total porosity that is measured in a tool having axial motion can be too low, and the measured $T_2$-distribution is generally distorted, mainly for the longer $T_2$ components.

Similar considerations are present in the radial direction due to radial fluid flow into the borehole. A result of the radial inflow of fluid is an outflow of polarized nuclei from the region of examination, as for the case of vertical tool movement discussed above. By reducing the field gradient, the "outflow effect" can be reduced. In the present disclosure, the tool is designed in such a way as to maintain close to a zero static field gradient in the radial direction, thus minimizing radial motion effects in the NMR signal. In addition to the outflow effect, motion causes a distortion of the phases of the NMR signals, which also reduces the amplitude of the received NMR signal. The phase distortion can be reduced by reducing the static magnetic field gradient but also by reducing the interecho time TE.

A similar solution can be used for a different problem, that of making NMR measurements in small boreholes. A BHA designed for use in a small borehole is limited to a small magnet size, so that a normal tool would have a small region of investigation. With small sensitive regions it is difficult to achieve a sufficient signal to noise ratio, which is required to have a high accuracy of the measurement combined with a good vertical resolution. In addition to or instead of expanding the radial extent of the zone of near zero field gradient, one embodiment of the disclosure combines multiple resonance areas to one big sensitive region, where the measurement is carried out. This combination can be done by designing one common antenna covering all areas.

Figure 3:
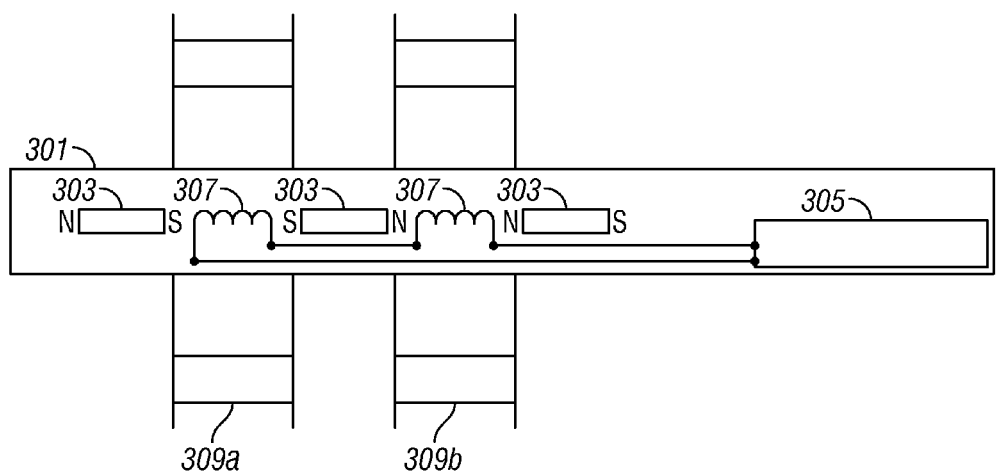
FIG. 3 shows an NMR sensor having multiple regions of examination.

FIG. 3 shows an exemplary logging tool 301. Three magnets 303 are shown. Adjacent magnets have like poles facing each other so as to define two regions of examination 309a, 309b. Antennas 307 are used for generating the RF pulses and measuring the spin echo signals. The electronics module 305 that includes a processor is used for processing the signals received by the antennas. In the configuration shown, the signals from the two antennas are summed, so that effectively, signals from a region of examination that is a combination of 309a and 309b are obtained. This increases the signal to noise ratio, but also reduces the vertical resolution of the NMR measurements. For the purposes of the present disclosure, the BHA may be considered to be a "carrier" and the magnet assembly produces a static magnetic field in one or more regions of examination. The static field gradient in the region of examination is nearly zero, so that during the length of the pulse sequence given by eqn. (1), the "outflow" effect is small and signals are obtained from nuclear spins that have been polarized. Another factor to be considered is that the outflow during the time TE should also be small, so that the spin echo signals are without phase distortion.

It is to be noted that the example given in FIG. 3 is directed towards the problem of obtaining an adequate signal in a small borehole. Basically the same design with a single region of examination can be used to address the problem of fluid inflow by selecting the combination of field gradient, and echo train length to satisfy the outflow condition.

In an alternate embodiment of the disclosure, using two independent antennas, the spin echo signals from 309a and 309b are stored separately in the electronics module. Depth determinations may be conveniently made by having synchronized clocks downhole and upholem and measuring the length of the drill string at the surface. When drilling has progressed so that the measurements made in one region of examination (say 309b) are at the same depth as those made earlier in the other region of examination (say 309a), then the data corresponding to the same depth are combined. This method of summing data from the same depth increases the signal to noise ratio without reducing the vertical resolution.

Figure 4A:
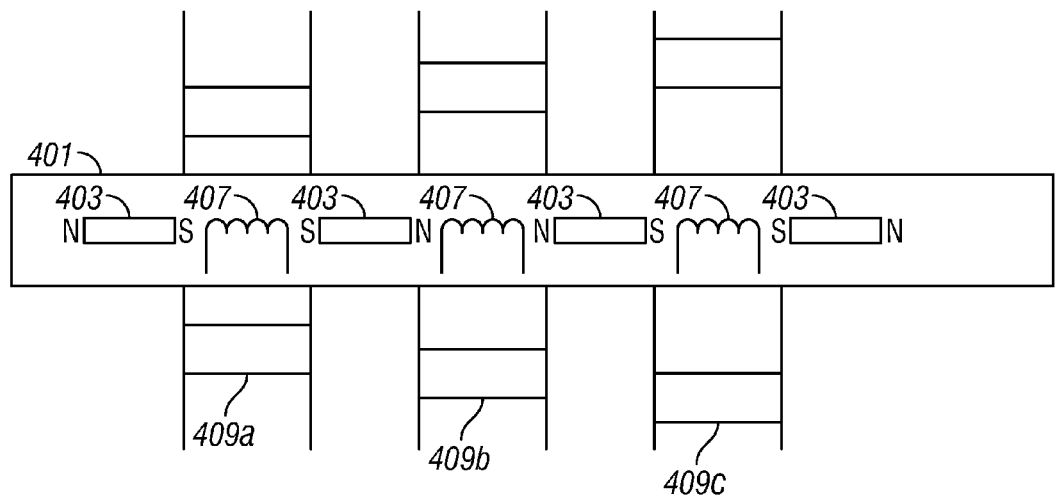
FIG. 4(a) shows an NMR sensor having axially spaced apart multiple regions of examination of different depths into the formation.

If the formation contains gas which is flowing to the borehole because the pressure in the borehole is lower than the pressure in the formation, we may measure the NMR-properties in a transient zone. Applying a tool with several resonance areas as shown in FIG. 4, having different depths of investigation, would allow characterizing the transition zone. Shown in FIG. 4a is a tool with three regions of investigation 409a, 409b and 409c that can be obtained using a tool 401 having four magnets 403 and three RF coils 407. Different depths of investigation can be obtained by changing the static magnetic field (using different magnet configurations)

Figure 4B:
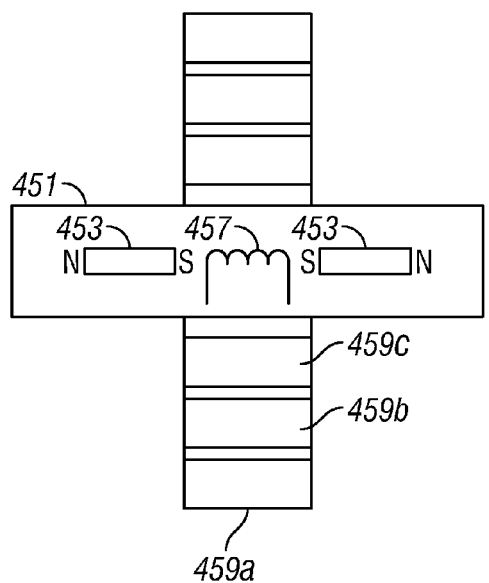
FIG. 4(b) shows an NMR sensor having multiple regions of examination of different depths into the formation a the same axial depth.

In an alternate design shown in FIG. 4(b), a pair of magnets 453 and one antenna 457 can be configured to get NMR signals from a multitude of sensitive regions 459a, 459b, 459c having different radial depths of investigation. The different sensitive regions may be selected by using different carrier frequencies for the radio-frequency magnetic field.

Figure 5:
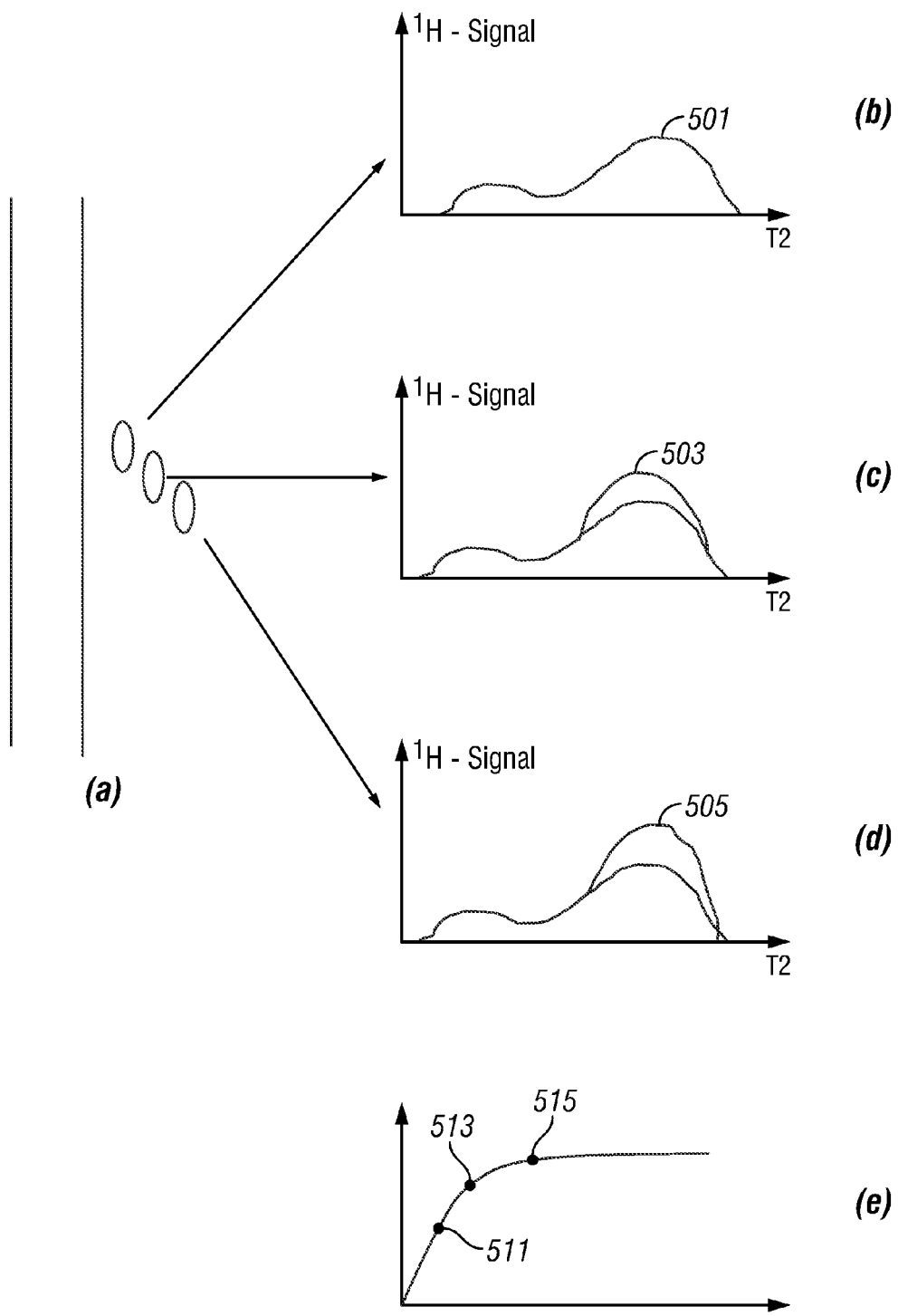
FIG. 5 shows three different regions of examination from which $T_2$ distributions are obtained and shown schematically by 501, 503 and 505 in (a), (b) and (c), and the estimate NMR porosity versus depth of investigation shown in (e)

Measurements made in the different regions can be used to yield a good estimate of formation properties. If the formation contains gas which is flowing to the borehole because the pressure in the borehole is lower than the pressure in the formation, we may measure the NMR-properties in a transient zone. This is illustrated in FIG. 5. FIG. 5(a) shows three different regions of examination. FIG. 5(b) shows an exemplary $T_2$ distribution 501 estimated from signals from the first region, FIG. 5(c) shows an exemplary $T_2$ distribution 503 estimated from signals from the second region, and FIG. 5(d) shows an exemplary $T_2$ distribution 505 estimated from signals from the third region. FIG. 5(e) shows estimated porosities 511, 513, 515 from FIGS. 5(b), 5(c) and 5(d) respectively plotted as a function of distance from the borehole. The radial variation of estimated porosity is, of course, not real. The NMR signal amplitude decreases near the borehole due to a formation of gas bubbles. This appears as an apparent porosity decrease, while, in fact, it is the hydrogen index of the fluid that decreases on approaching the borehole. Extrapolation of these estimated porosities away from the borehole gives an estimate of the true porosity of the formation.

Figure 6:
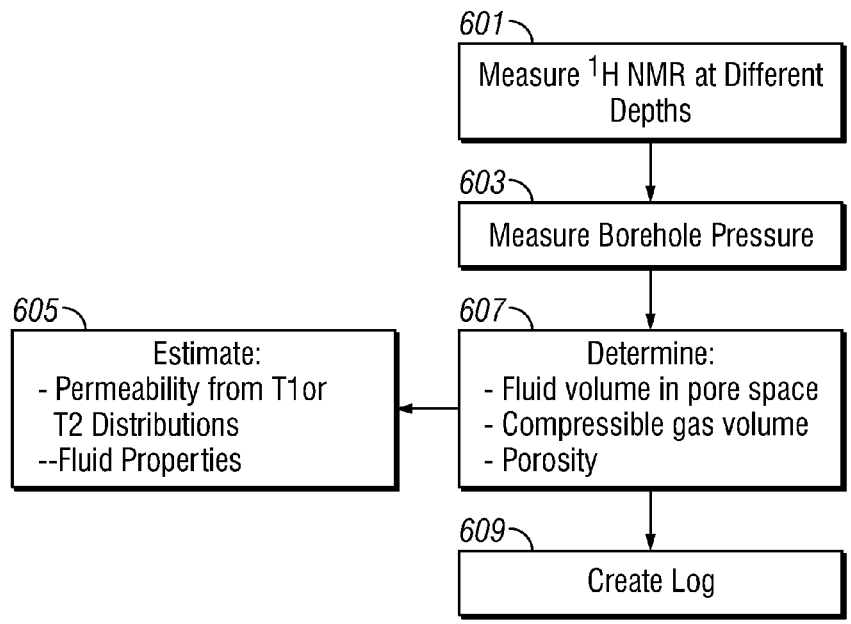
FIG. 6 shows a flow chart for estimating different formation properties using NMR measurements from different depths of investigation.

Turning to FIG. 6, a schematic flow chart illustrates different formation properties that can be estimated from NMR measurements at different depths of investigation. NMR measurements are made at a plurality of depths of investigation 601 and the borehole pressure is measured 603. From these, it is possible to estimate the formation permeability from $T_1$ or $T_2$. The permeability can be estimated using Coates' method, or a value from an offset well may be used. It is also possible to determine the fluid volume in the pore space, compressible gas volume and porosity at each of the depths of investigation and extrapolate to the formation away from the borehole as discussed above: methods for estimation of water saturation, oil saturation, gas saturation and porosity from $T_2$ distributions are known in prior art. By making these measurements at different axial depths of the BHA, a log of each of these properties can be obtained even while drilling with underbalanced mud borehole pressure. Of particular interest with underbalanced drilling is the ability to identify a radial distance from the borehole at which the formation fluid reaches the bubble point. This manifests itself in a non-zero gas saturation or a reducing apparent porosity. When the bubble point is reached far from the borehole, this is a warning signal that a potential gas kick could be large and, as a remedial measure, the mud weight should be increased.

Figure 7:
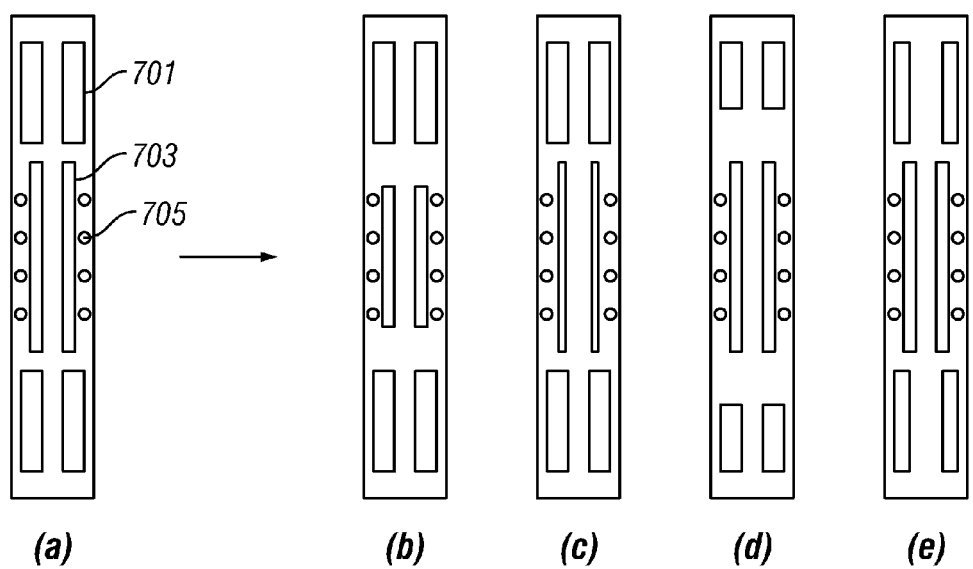
FIGS. 7(a)-(e) shows different hardware configurations to reduce the radial field gradient.

Turning now to FIG. 7, different hardware modifications to the basic tool of FIG. 2 are discussed to increase the radial size of the region of investigation. FIG. 7(a) shows the important components of the NMR tool. They are the permanent magnets 701, the soft magnetic antenna core 703 and the RF antenna 705. In FIG. 7(b), the length of the antenna cores is reduced relative to the length in FIG. 7(a). In FIG. 7(c), thickness of the antenna cores is reduced relative to FIG. 7(a). In FIG. 7(d), the gap between the magnets and the antenna core is increased relative to FIG. 7(a). In FIG. 7(e), the gap between the magnets and the antenna core are the same as in FIG. 7(a) while the cross sectional area of the magnets is reduced. All of these design modifications result in different sizes of the region where the magnetic field gradient is near zero.

The disclosure has been described with reference to a NMR device that is part of a BHA conveyed on a drillstring. The disclosure is equally applicable for NMR devices conveyed on coiled tubing. The processing described herein may be done using a downhole processor and the results stored on a suitable memory downhole or telemetered to the surface. Alternatively, the data may be stored on a downhole memory and processed when the BHA is tripped out of the borehole. With improved telemetry capability, it should be possible to telemeter the NMR measurements to a surface location and do the processing there.

The results of the processing may be used to estimate, using known methods, properties of interest such as a $T_2$ distribution, volumetrics, permeability, bound volume irreducible, effective porosity, bound water, clay-bound water, total porosity, pore size distribution, and other rock and fluid properties that are based on NMR data. These are all used in reservoir evaluation and development.

The processing of the data may be conveniently done on a processor. The processor executes a method using instructions stored on a suitable computer-readable medium product. The computer-readable medium may include a ROM, an EPROM, an EAROM, a flash memory, and/or an optical disk.

While the foregoing disclosure is directed to the specific embodiments of the disclosure, various modifications will be apparent to those skilled in the art. It is intended that all such variations within the scope and spirit of the appended claims be embraced by the foregoing disclosure.

What is claimed is:

1. An apparatus configured to evaluate an earth formation, the apparatus comprising:
a carrier configured to be conveyed in a borehole in the earth formation;
a magnet assembly on the carrier configured to produce a static magnetic field in the earth formation and to define a plurality of regions of examination at different radial distances from the borehole;
at least one antenna on the carrier configured to be activated with at least one pulse sequence, the at least one pulse sequence configured to produce a signal from nuclear spins from an associated one of the plurality of regions of examination; and
a processor configured to estimate a value of a property of the earth formation at the different radial distances using the produced signal from each of the plurality of regions of examination.

2. The apparatus of claim 1 wherein the pulse sequence is of the form:

$$TW-TP-\tau_1-(RP-\tau_2-echo-\tau_2)_n$$

wherein TW is a (long) wait time of several times a spin lattice relaxation time, TP is a tipping pulse for tipping the nuclear spins at an angle substantially equal to 90° to cause precession thereof, $\tau_1$, $\tau_2$ are waiting times, RP is a refocusing pulse for tipping the nuclear spins greater than 90° and n is the number of echoes to be acquired in one sequence.

3. The apparatus of claim 1 wherein the plurality of regions are axially spaced apart along the borehole.

4. The apparatus of claim 1 wherein the plurality of regions are at substantially the same axial position along the borehole and wherein the at least one pulse sequence further comprises a plurality of pulse sequences each having an associated frequency.

5. The apparatus of claim 1 wherein a length of the at least one pulse sequence is selected to suppress the effect on the produced signal due to a fluid flow caused by an excess of a formation fluid pressure over a borehole fluid pressure.

6. The apparatus of claim 1 wherein an interecho time TE of the pulse sequence is selected to suppress the effect on the produced signal due to a fluid flow caused by an excess of a formation pore pressure over a fluid pressure in the borehole.

7. The apparatus of claim 1 wherein the estimated value of the property further comprises an apparent porosity and the processor is further configured to use the estimated value of the apparent porosity for at least one of: (i) estimating a fluid saturation in the formation away from the borehole, (ii) producing a signal indicative of a gas kick, and (iii) estimating a true porosity of the earth formation.

8. The apparatus of claim 7 wherein the processor is further configured to estimate a value of a property of the earth formation selected from:
(i) $T_2$ distribution, (ii) volumetrics, (iii) a permeability, (iv) a bound volume irreducible, (v) effective porosity, (vi) bound water, (vii) clay-bound water and (viii) total porosity.

9. The apparatus of claim 1 wherein the carrier further comprises a bottomhole assembly configured to be conveyed on a drilling tubular into the borehole.

10. A method of evaluating an earth formation, the method comprising:
conveying a carrier into a borehole in the earth formation;
using a magnet assembly on the carrier to produce a static magnetic field in the earth formation and to define a plurality of regions of examination at different radial distances from the borehole;
activating at least one antenna on the carrier with at least one pulse sequence, the at least one pulse sequence configured to produce a signal from nuclear spins from an associated one of the plurality of regions of examination; and
using a processor for estimating a value of a property of the earth formation at the different radial distances using the produced signal from each of the plurality of regions of examination.

11. The method of claim 10 wherein the pulse sequence is of the form:

$$TW-TP-\tau_1-(RP-\tau_2-echo-\tau_2)_n$$

wherein TW is a (long) wait time of usually several times a spin lattice relaxation time, TP is a tipping pulse for tipping the nuclear spins at an angle substantially equal to 90° to cause precession thereof, $\tau_1$, $\tau_2$ are waiting times, RP is a refocusing pulse for tipping the nuclear spins greater than 90° and n is the number of echoes to be acquired in one sequence.

12. The method of claim 10 further comprising using the magnet assembly for defining the plurality of regions as axially spaced apart along the borehole.

13. The method of claim 10 further comprising:
using the magnet assembly for defining the plurality of regions at substantially the same axial position along the borehole; and
using, for the at least one pulse sequence, a plurality of pulse sequences each having an different associated frequency.

14. The method of claim 10 further comprising selecting a length of the at least one pulse sequence for suppressing the effect on the produced signal due to a fluid flow caused by an excess of a formation pore pressure over a borehole fluid pressure.

15. The method of claim 10 further comprising selecting an interecho time TE of the pulse sequence for suppressing the effect on the produced signal due to the fluid flow caused by an excess of a formation pore pressure over a fluid pressure in the borehole.

16. The method of claim 10 wherein the estimated value of the property further comprises an apparent porosity, the method further comprising:
using the processor for at least one of: (i) estimating a fluid saturation in the formation away from the borehole, (ii) producing a signal indicative of a gas kick, and (iii) estimating a true porosity of the earth formation.

17. The method of claim 16 further comprising altering a mud weight used for drilling operations.

18. The method of claim 10 further comprising:
using, as the carrier, a bottomhole assembly; and
conveying the bottomhole assembly on a drilling tubular into the borehole.

* * * * *